United States Patent [19]

Jett-Tilton

[11] Patent Number: 4,997,761

[45] Date of Patent: Mar. 5, 1991

[54] PHOSPHATIDYL TREATMENT OF VIRAL DISEASE

[75] Inventor: Marti Jett-Tilton, Washington, D.C.

[73] Assignee: Houston Biotechnology Incorporated, The Woodlands, Tex.

[21] Appl. No.: 106,615

[22] Filed: Oct. 6, 1987

[51] Int. Cl.$^5$ .................. C12N 5/00; A61K 31/00; A61K 37/00

[52] U.S. Cl. .................. 435/240.2; 435/235.1; 424/450; 514/78; 436/829

[58] Field of Search .................. 435/240.2, 235; 424/450; 436/829; 514/78

[56] References Cited

U.S. PATENT DOCUMENTS 4,666,893 5/1987 Tsuichya .................. 514/78

FOREIGN PATENT DOCUMENTS 57082311 11/1980 Japan.
61024519 11/1984 Japan.

OTHER PUBLICATIONS

"A Special Lipid Mixture for Membrane Fluidization", by Lyte et al. in *Biochimica et Biophysica Acta* (1985), 812:133–138.

"Effects of a Novel Compound (AL721) on HTLV-III Infectivity in Vitro", by Sarin et al., in *New England Journal of Medicine*, (1985) 313: No. 20.

"AL721, A Novel Membrane Fluidizer", by Antonian et al. in *Neuroscience and Biobehavioral Reviews* (1987) 11:399–413.

Schlegel et al., *Cell 32:639–646, 1983*, "Inhibition of VSV Binding and Infectivity by Phosphatidy/Serine: Is Phosphatidy/Serine a VSV-Binding Site?".

Jett et al., *B B Res Comm* 114: 863–871, 1983, "Selective Cytotoxicity of tumor Cells Induced by Liposomes Containing Plant Phosphatidylinositol".

Norley et al. *J. Immun./36*: 681–685, 1986, "Targeting of Drug Loaded Immunoliposomes to HSV Infected Corneal Cells: An Effective Means of Inhibiting Virus Replication In Vitro".

*Primary Examiner*—Charles F. Warren
*Assistant Examiner*—Jasemine C. Chambers
*Attorney, Agent, or Firm*—Barbara Rae-Venter; Bertram I. Rowland

[57] ABSTRACT

Phosphatides are shown to have antiviral activity, where the phosphatides are characterized by having a polyunsaturated fatty acid at the sn2 position. By contacting cells susceptible to or infected with a virus, particularly a retrovirus, the proliferation of the virus is substantially inhibited.

18 Claims, No Drawings

PHOSPHATIDYL TREATMENT OF VIRAL DISEASE

INTRODUCTION

1. Technical Field

The field concerns the treatment of viral diseases employing polyunsaturated fatty acid glycerides and derivatives thereof.

2. Background

Viral infections are particularly difficult to treat. In order for viruses to survive, the viruses have developed many mechanisms to elude the host defenses. The viruses may be highly polymorphic, so that the immune system cannot recognize different strains, leaving the host subject to repetitive infection by the various strains. The virus may be subject to mutation, so that the viral antigens over the course of the infection change, preventing the immune system from responding to the virus due to the varying nature of the antigenic proteins presented to the host. In cases of such viruses, the host has a difficult time to respond to the infection.

In addition, the virus is parasitic in requiring the use of the host cell's, metabolism and enzymes for proliferation. Since the cellular mechanisms are involved with viral proliferation, it is difficult to be able to treat the host to prevent proliferation, without also affecting the host's cells. Viral drugs are frequently associated with the rapid rate of replication of the virus as compared to the host cell to inhibit the virus. Inevitably, the host cell also is inhibited from DNA replication, which seriously affects those rapidly multiplying host cells, such as the hematopoietic system.

A further difficulty with protection against viral diseases is that the virus spends a substantial portion of its lifetime within the cell, to some degree protected from the host immune system. While the host has developed the ability to recognize viral proteins on the cell surface and kill viral invaded cells, the ability of the virus to remain in the cell and proliferate prior to cellular death, enhances the viral capability to maintain an infectious state.

It is therefore of substantial interest to be able to develop therapeutic treatments which enhance the host's ability to respond to a viral infection.

Relevant Literature

Jett et al., *Biochem. Biophys. Res. Commun.* (1983) 114: 863–871, incorporated herein by reference discloses that liposomes containing plant phosphatidyl inositol (PI), cholesterol and cholesteryl oleate selectively killed tumor cells from cultured cell lines without harming the normal cells present. Certain synthetic phosphatidyl inositols were found to be equally effective as the plant PI. Jett et al., *Cancer Research* (1985) 45: 4810–4815.

SUMMARY OF THE INVENTION

Prophylactic or therapeutic amounts of phosphatides or phosphatidyl derivatives are administered to a host for viral treatment. The phosphatides are characterized by being triesters, having carboxylates at the sn1 and sn2 positions, where the carboxylate at the sn2 position is at least about 10 carbon atoms and has at least 2 sites of aliphatic unsaturation, where the sn3 position has a phosphate, which phosphate may be substituted or unsubstituted on oxygen.

DESCRIPTION OF THE SPECIFIC EMBODIMENTS

Mammalian hosts are treated with a prophylactic or therapeutic dose of a phosphatide to prevent the proliferation of virus in the host. The phosphatide is characterized by having at least 17 carbon atoms and usually fewer than 60 carbon atoms, more usually fewer than about 40 carbon atoms, where the sn1 and sn2 positions are substituted with carboxylic acids, the sn2 position having a carboxylic acid having at least 2 aliphatic sites of unsaturation, usually olefinic sites.

For the most part, the phosphatides will be phospholipase $A_2$ substrates and have the following formula:

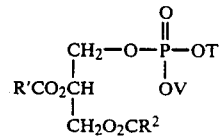

wherein:

T is hydrogen, physiologically acceptable counterion, e.g. salt, such as sodium, potassium, calcium, etc., inositol, any of its phosphate derivatives, mono-, di- or tri-, including cyclic phosphate, choline, serine, ethanolamine, glycerol, or other group which does not interfere with phospholipase $A_2$ activity;

V is hydrogen or a physiologically acceptable counterion;

$R'CO_2$ is a polyunsaturated aliphatic fatty acid of at least about 10 carbon atoms, preferably at least about 12 carbon atoms, usually not more than about 36 carbon atoms, more usually not more than about 28 carbon atoms, having at least 2 sites of aliphatic unsaturation and may have 6 or more, usually not more than 5, more usually not more than 4, generally from 2 to 4 sites of aliphatic unsaturation;

$R^2CO_2$ is a fatty acid of at least 2 carbon atoms and not more than about 36 carbon atoms, generally ranging from about 2, usually 12 to 24 carbon atoms, and may be saturated or unsaturated, having from 0 to 5, usually 0 to 4, more usually 0 to 3 sites, generally 0 to 1 of aliphatic unsaturation.

The aliphatic unsaturation may be at any site in the fatty acid and may be ethylenic or acetylenic, conjugated or unconjugated, preferably conjugated, naturally occurring or synthetic. There may be from 0 to 2, usually 0 to 1 substituents, particularly oxy, e.g. hydroxyl. The chains may be branched or straight chain, usually straight. For the unsaturated acids, unsaturated acids include linoleic, α- or γ-linolenic, arachidonic, geranic, 9,11-octadecatrienoic acid, dehydrogeranic acid, elaeostearic acid, 6,9,12-octadecatrienoic, stearidonic, clupanadonic, etc. For the saturated or monounsaturated fatty acids, the acids include acetic, propionic, butyric, lauric, myristic, palmitic, palmitoleic, oleic, stearic, etc.

The subject compound may be a single composition or a mixture of compounds, as to the lipids at the 1 and 2 positions (phosphate being the 3 position), or as to the substituent bound to phosphate. Conveniently, naturally occurring compositions may be employed such as plant compositions, such as soybean, rape seed, safflower, corn, sunflower, etc., as the inositols, glycerols, chlolines, etc. The naturally occurring compositions may be extracted, purified, fractionated, or subjected to other treatment.

Specific compounds of interest include sn-3-phosphatidyl-1-palmitoyl-2-linolenoyl (or linoleoyl) inositol; sn-3-phosphatidyl-1-acetyl-2-arachidonyl choline; sn-3-phosphatidyl-1-butyryl-2-eicosatetraenoyl inositol-4-phosphate; sn-3-phosphatidyl-1-lauryl-2-linoleoyl ethanolamine. The subject compounds may be obtained from any source, including plant glycerides, fish glycerides, may be prepared synthetically, or combinations thereof.

The subject compositions may be used by themselves or in conjunction with other fatty acids, particularly when prepared as vesicles or liposomes. Where prepared as liposomes, the subject compositions will be at least about 5 mole percent, more usually at least about 25 mole percent and preferably in the range of about 50 to 80 mole percent, more preferably in the range of about 55 to 75 mole percent. Desirably, the subject compositions should be free of phosphatides which have a saturated or mono-olefinic carboxylic acid at the sn2 position. The liposomes may be made in accordance with conventional ways, by combining the various lipids, evaporating solvent, suspending the dried lipid in an aqueous medium, and subjecting the medium to rapid agitation, for example, by ultrasonic sound. Other lipids which may be used include cholesterol polyunsaturated fatty acid esters, e.g. methyl esters, etc. The resulting vesicles may then be isolated and used. See, for example, Kim and Martin, *Biochem. et Biophys. Acta* (1981) 646: 1-9 and U.S. Pat. Nos. 4,311,712; 4,310,506; 4,302,459; 4,261,975; 4,241,046; 4,235,871; 4,229,360; 4,224,179; 4,053,385; 4,016,290 and 3,957,971.

If desired, the liposomes may be modified to direct the liposomes to particular types of cells using site directing molecules. Thus, antibodies or ligands for particular receptors may be employed, where the target cell is associated with a particular surface protein. For example, with the AIDS virus, the AIDS virus is primarily directed to cells having the CD4 surface protein. By having anti-CD4 bound to the surface of the liposome, the liposome may be directed primarily to T-helper cells.

The particular ligand or antibody may be conjugated to the liposome in accordance with conventional ways, either by conjugating the site directing molecule to a lipid for incorporation into the lipid bilayer or by providing for a linking group on a lipid present in the bilayer for linking to a functionality of the site directing compound.

The subject compositions may be formulated in a wide variety of ways, employing physiologically acceptable media, such as deionized water, phosphate buffered saline, Ringers solution or other appropriate solution. The amount of the active phosphatide may vary widely in the medium, generally ranging from about 100 mg/ml to 1 mg/ml. Depending upon the manner of administration, the frequency, the nature of the target, and the like, usually from about 0.5 mg to 800 mg of the phosphatide will be used per kg of host, inversely related to the weight of the host. Other compositions may be present, such as stabilizers, buffers to provide a physiological pH, e.g. 6-8.5, or the like.

The subject compositions may be used for treatment of a variety of viral diseases, such as treatment of lentiviruses, e.g. HIV, papilloma, influenza, herpes, or the like.

The subject compositions may be used by themselves or in conjunction with other drugs for the treatment of viral diseases. Where the subject compositions have been prepared as liposomes, other drugs may be included in the lumen of the liposome, so as to be delivered at the same time to the cell and may be subject to endocytosis. Drugs of interest include cytotoxic drugs, drugs inhibiting DNA replication, etc. Various drugs which may find use include methotrexate, $\gamma$-interferon, azidothymidine, azidocytidine, vinca alkaloids, adriamycin, dideoxyadenosine or derivatives thereof, 5-fluorouracil, ribovirin, acyclovir, and cytokines. These drugs will be used at concentrations in accordance with normal administration or in smaller amounts where the combined effect of the phosphatides and ancillary drug provide the therapeutic result with lesser amounts.

The subject compounds are found to be effective in inhibiting the proliferation of viruses intracellularly, while having little or no effect on normal cells. Thus, the subject compounds may be administered systemically by injection into the vascular system, parenterally, by inhalation, orally, or the like. The particular manner of administration may vary with the site of the virus, whether the administration is prophylactic or therapeutic, the dosage level, or the like.

The subject compositions may also be used in vitro to inhibit viral infection in cell cultures, compare activities of viruses, elucidate the mechanism of viral replication and the use of cellular processes, and the like.

The following examples are offered by way of illustration and not by way of limitation.

EXPERIMENTAL

In order to establish the effect of plant phosphatidyl esters as inhibitors of viral growth, the following study was carried out. For use as the esters, soybean phospholipids were employed which are 52% phosphatidyl inositol, 21% phosphatidylserine and 27% phosphatidyl ethanolamine. The mixture was called PL. It was combined with cholesterol in a 2:1 molar ratio with soybean phosphatidylinositol esters, which contain fatty acids consisting of palmitic, 38.7%; linoleic, 48.9%; oleic, 4.8%; and stearic, 7.6%, where the sn2 position is primarily linoleic.

The following are the procedures and materials employed.

Negative Control

A. Target cells incubated in CM-1 (RPMI-1640 medium containing 10% fetal calf serum, 100 units of penicillin G potassium, 100 mcg streptomycin sulphate and 2 mM glutamine).

B. Target cells incubated in 500 nmoles/ml soybean phosphatidyl inositol (PL).

Positive Control

Target cells incubated in $10^{-4}$ to $10^{-7}$ dilutions of HIV-I ($\sim 6$ log$_{10}$ TCID$_{50}$/ml). (Tissue Culture Infective Dose.)

Methods and Procedures

A. Condition #1: Pre-treatment of H9 cells with PL

1. $20 \times 10^6$ H9 cells were incubated overnight in 20 ml of 500 nmoles/ml PL.

2. Cells were pipetted into two centrifuge tubes (10 mls each) and centrifuged to obtain cell pellets.

3. Each cell pellet was resuspended in 1 ml of $10^{-3}$ dilution of HIV-I and incubated at 37° C., 90 minutes for virus adsorption.

4. Following virus adsorption, cells were washed once with medium, the test pellet was resuspended in 20 ml of CM-1. Each cell suspension was distributed to 4 $T_{30}$ flasks (5 ml/flask).

B. Condition #2: No prior treatment of H9 cells; PL and HIV-I applied together

1. Two tubes of condition #2-1 each with 1.0 ml $10^{-3}$ dilution of HIV-I containing 500 nmoles/ml PL and two tubes of condition #2-2 each with 1.0 ml $10^{-3}$ dilution HIV-I containing 350 nmoles/ml PL were incubated at room temperature for 1 hour.

2. Contents of each tube were used to resuspend $10 \times 10^6$ DEAE-dextran treated (20 μg/ml, 20 minutes at 37° C.), H9 cells and inbubated at 37° C., 90 minutes for virus adsorption.

3. Following incubation, cells were washed once with medium, and cells from one tube of conditions #2-1 (test) were resuspended in 20 ml of CM-1 containing 500 nmoles/ml PL and cells from one tube of condition #2-2 (test) were resuspended in 20 ml CM-1 containing 350 nmoles/ml PL. Control cells of condition #2-1 and condition #2-2 were resuspended in 20 ml of CM-1. Each cell suspension was distributed to 4 $T_{30}$ flasks (5 ml/flask).

C. Condition #3: Post-treatment of HIV-I-infected H9 cells with PL

1. Two pellets of $10 \times 10^6$ DEAE-deatran treated H9 cells were resuspended in 1.0 ml $10^{-3}$ dilution of HIV-I and incubated at 37° C., 90 minutes for virus adsorption.

2. Following incubation, cells were washed once with medium and each cell pellet was resuspended in 20 ml CM-1 and incubated in two $T_{60}$ flasks for 48 hours.

3. Following a second incubation, the cells were removed from the flasks and centrifuged to obtain cell pellets. Test cells were resuspended in 20 ml CM-1 containing 500 nmoles/ml PL and control cells in 20 ml CM-1. Each cell suspension was distributed to 4 $T_{30}$ flasks.

D. Controls

1. Serial 10-fold dilutions of HIV-I were performed in CM-1 and 1.0 ml each of $10^{-4}$ to $10^{-7}$ dilutions were used to resuspend $10 \times 10^6$ DEAE-dextran treated H9 cells (Positive control). For toxicity control, 1.0 ml 500 nmoles/ml PL in CM-1 were used to resuspend $10 \times 10^6$ H9 cells and for negative control 1.0 ml CM-1 was used to resuspend $10 \times 10^6$ H9 cells.

2. Cell suspensions were incubated at 37° C., 90 minutes for virus adsorption, washed with medium, each cell pellet was resuspended in 20 ml CM-1 and distributed to 4 $T_{30}$ flasks.

E. Monitoring of Cultures

1. Cultures were monitored for 4 weeks for viable cell number, characteristic cytopathic effect (CPE) and for release of virus as determined by precipitable reverse transcriptase assay. Two ml was removed from each culture and test cultures were replaced with 3.0 ml CM-1 containing PL and control cultures were replaced with 3.0 ml CM-1 each week.

Criteria for a Valid Test

The test is considered valid if, (1) positive control target cells exhibit characteristic CPE, (2) the counts per minute (CPM) in the reverse transcriptase assay (dT.rA counts) are less than 10,000 in the negative control, and the positive control has CPM's greater than 10,000.

TABLE A

Results - Observation of Cultures

| Group | Description | Day 7 | Day 14 | Day 21 | Day 28 |
|---|---|---|---|---|---|
| Condition #1 | | | | | |
| Test A | Pre-treatment of H9 cells | MG | MG | MG | MG |
| B | with 500 nmoles/ml PL overnight, | LG | MG,CPE+ | MG,CPE+ | MG |
| C | virus absorption and cultured | LG | MG | HG,CPE+ | MG |
| D | in 500 nmoles/ml PL | LG | MG,CPE+ | HG,CPE+ | MG |
| Control A | Pre-treatment of H9 cells | MG | HG,CPE+++ | HG,CPE+++ | HG,CPE++ |
| B | with 500 nmoles/ml PL overnight, | MG | HG,CPE+++ | HG,CPE+++ | HG,CPE++ |
| C | virus absorption and cultured | MG | HG,CPE+++ | HG,CPE+++ | HG,CPE+++ |
| D | in CM-1 | MG | HG,CPE+++ | HG,CPE+++ | HG,CPE+++ |
| Condition #2-1 | | | | | |
| High Dose | | | | | |
| Test A | 500 nmoles/ml PL + virus 1 hour | LG | MG,CPE+ | HG,CPE+ | Contaminated |
| B | virus absorption on H9 | LG | HG,CPE+ | HG,CPE+ | MG |
| C | cells and cultured in | LG | MG,CPE+ | HG,CPE+ | MG |
| D | 500 nmoles/ml PL | LG | MG | HG,CPE+ | MG |
| Control A | 500 nmoles/ml PL + virus 1 hour | MG,CPE+ | HG,CPE+++ | HG,CPE+++ | HG,CPE+ |
| B | virus absorption in H9 | MG,CPE+ | HG,CPE++ | HG,CPE++ | HG,CPE++ |
| C | cultured in CM-1 | MG,CPE+ | HG,CPE+++ | HG,CPE+++ | HG,CPE+++ |
| D | | MG,CPE+ | HG,CPE+++ | HG,CPE+++ | HG,CPE+ |
| Condition #2-2 | | | | | |
| Test A | 350 nmoles/ml PL + virus 1 hour | MG | MG,CPE+ | MG | MG |
| B | virus absorption on H9 | MG | MG,CPE+ | HG,CPE+ | MG |
| C | cells and cultured | MG | MG,CPE+ | MG | MG |
| D | 350 nmoles/ml PL | MG | MG,CPE+ | HG,CPE+ | HG |
| Control A | 350 nmoles/ml PL + virus 1 hour, | MG,CPE+ | HG,CPE+++ | HG,CPE+++ | HG,CPE++ |
| B | virus absorption on H9 cells | MG,CPE+ | HG,CPE+++ | HG,CPE+++ | HG,CPE++ |
| C | and cultured in CM-1 | MG,CPE+ | HG,CPE+++ | HG,CPE+++ | HG,CPE++ |
| D | | MG,CPE+ | HG,CPE+++ | HG,CPE+++ | HG,CPE+++ |
| Condition #3 | | | | | |
| Test A | Virus infect H9 cells for | MG | MG,CPE+ | MG,CPE+ | MG |
| B | 48 hours, then cultured | MG | MG,CPE+ | MG,CPE+ | MG |
| C | in 500 nmoles/ml PL | MG | MG,CPE+ | MG | MG |

TABLE A-continued

Results - Observation of Cultures

| Group | Description | Day 7 | Day 14 | Day 21 | Day 28 |
|---|---|---|---|---|---|
| D | | MG | MG,CPE+ | MG | MG |
| Control A | Virus infect H9 cells for 48 | MG,CPE++ | HG,CPE+++ | HG,CPE+++ | HG,CPE+++ |
| B | hours, then cultured in CM-1 | MG,CPE++ | HG,CPE+++ | HG,CPE+++ | HG,CPE++ |
| C | | MG,CPE++ | HG,CPE+++ | HG,CPE+++ | HG,CPE++ |
| D | | MG,CPE++ | HG,CPE+++ | HG,CPE+++ | HG,CPE+++ |
| Positive Control | | | | | |
| HIV-I $10^{-4}$ A | H9 cells infected with virus | MG,CPE+ | HG,CPE+++ | HG,CPE++ | HG,CPE+++ |
| B | and cultured in CM-1 | MG | HG | HG | HG |
| C | | HG | HG,CPE+ | HG,CPE++ | HG,CPE+++ |
| D | | MG | HG,CPE+ | HG,CPE++ | HG,CPE+++ |
| $10^{-5}$ A | | HG | HG | HG | HG |
| B | | MG | HG | HG | HG,CPE+ |
| C | | MG | HG | HG | HG,CPE+ |
| D | | MG | HG | HG | HG |
| $10^{-6}$ A | H9 cells infected with virus | MG | HG | HG | HG |
| B | and cultured in CM-1 | MG | HG | HG | HG |
| C | | MG | HG | HG | HG |
| D | | MG | HG | HG | HG |
| $10^{-7}$ A | | MG | HG | HG | HG |
| B | | MG | HG | HG | HG |
| C | | MG | HG | HG | HG |
| D | | MG | HG | HG | HG |
| Toxicity Control | | | | | |
| A | H9 cells cultured in | LG | MG | MG | HG |
| B | 500 nmoles/ml PL | LG | MG | MG | HG |
| C | | LG | MG | MG | HG |
| D | | LG | MG | MG | HG |
| Target Cell Control | | | | | |
| A | H9 cells cultured in CM-1 | MG | HG | HG | HG |
| B | | MG | HG | HG | HG |
| C | | MG | HG | HG | HG |
| D | | MG | HG | HG | HG |

VHG = Very Heavy Growth, >2 × $10^6$/ml
HG = Heavy Growth, 1-2 × $10^6$/ml
MG = Moderate Growth, 0.5-1 × $10^6$/ml
LG = Light Growth, <0.5 × $qp^6$/ml
DC = Dead Cells
CPE = Cytopathic Effect
+++ = Many
++ = Some
+ = Few

TABLE A.2

Results - Reverse Transcriptase

| | | CPM - dT.rA | | | | |
|---|---|---|---|---|---|---|
| Group | Description | Day 7 | Day 14 | Day 21 | Day 28 | TCID$_{50}$ |
| Condition #1 | | | | | | |
| Test A | Pre-treatment of H9 cells | 319 | 433 | 218 | 539 | Neg |
| B | with 500 nmoles/ml PL overnight, | 177 | 424 | 299 | 269 | |
| C | virus absorption and cultured | 304 | 435 | 321 | 259 | |
| D | in 500 nmoles/ml PL | 282 | 402 | 152 | 248 | |
| Control A | Pre-treatment of H9 cells | 1,235 | 93,050 | 96,314 | 271,277 | Pos |
| B | with 500 nmoles/ml PL overnight, | 1,795 | 261,512 | 358,437 | 439,554 | |
| C | virus absorption and cultured | 2,127 | 116,627 | 520,322 | 251,393 | |
| D | in CM-1 | 1,506 | 75,799 | 300,577 | 225,538 | |
| Condition #2-1 High Dose | | | | | | |
| Test A | 500 nmoles/ml PL + virus 1 hour | 128 | 811 | 676 | N/A** | Neg |
| B | virus absorption on H9 | 471 | 241 | 299 | 450 | |
| C | cells and cultured in | 210 | 293 | 105 | 291 | |
| D | 500 nmoles/ml PL | 482 | 244 | 520 | 306 | |
| Control A | 500 nmoles/ml PL + virus 1 hour | 2,971 | 185,535 | 564,979 | 264,612 | Pos |
| B | virus absorption in H9 | 754 | 4,206 | 437,475 | 273,384 | |
| C | cultured in CM-1 | 919 | 42,846 | 301,359 | 446,452 | |
| D | | 961 | 12,775 | 379,111 | 467,160 | |
| Condition #2-2 Low Dose | | | | | | |
| Test A | 350 nmoles/ml PL + virus 1 hour | 441 | 409 | 958 | 287 | Neg |
| B | virus absorption on H9 | 290 | 363 | 504 | 287 | |
| C | cells and cultured | 425 | 243 | 144 | 530 | |
| D | 350 nmoles/ml PL | 254 | 379 | 223 | 390 | |
| Control A | 350 nmoles/ml PL + virus 1 hour, | 714 | 49,613 | 378,246 | 365,697 | Pos |
| B | virus absorption on H9 cells | 1,659 | 198,003 | 326,734 | 479,547 | |

TABLE A.2-continued

Results - Reverse Transcriptase

| Group | | Description | CPM - dT.rA | | | | $TCID_{50}$ |
|---|---|---|---|---|---|---|---|
| | | | Day 7 | Day 14 | Day 21 | Day 28 | |
| | C | and cultured in CM-1 | 1,565 | 140,500 | 430,352 | 368,825 | |
| | D | | 754 | 72,545 | 334,856 | 499,048 | |
| Condition #3 | | | | | | | |
| Test | A | Virus infect H9 cells for | 251 | 211 | 520 | 383 | Neg |
| | B | 48 hours, then cultured | 188 | 201 | 217 | 328 | |
| | C | in 500 nmoles/ml PL | 220 | 194 | 702 | 212 | |
| | D | | 226 | 1,044 | 258 | 514 | |
| Control | A | Virus infect H9 cells for 48 | 686 | 238,111 | 420,869 | 299,287 | Pos |
| | B | hours, then cultured in CM-1 | 807 | 38,718 | 169,178 | 254,379 | |
| | C | | 845 | 138,041 | 304,458 | 312,629 | |
| | D | | 701 | 87,599 | 411,584 | 429,081 | |
| Positive Control | | | | | | | |
| HIV-I $10^{-4}$ | A | H9 cells infected with virus | 204 | 1,028 | 7,656 | 78,761 | $10^{4.25}$ |
| | B | and cultured in CM-1 | 246 | 560 | 347 | 616 | |
| | C | | 485 | 669 | 5,060 | 57,136 | |
| | D | | 926 | 1,405 | 21,233 | 146,505 | |
| $10^{-5}$ | A | | 451 | 413 | 559 | 902 | |
| | B | | 322 | 433 | 552 | 434 | |
| | C | | 228 | 452 | 452 | 2,178 | |
| | D | | 214 | 264 | 429 | 487 | |
| $10^{-6}$ | A | H9 cells infected with virus | 250 | 253 | 612 | 347 | |
| | B | and cultured in CM-1 | 684 | 170 | 2,191 | 605 | |
| | C | | 267 | 404 | 391 | 533 | |
| | D | | 189 | 355 | 215 | 462 | |
| $10^{-7}$ | A | | 555 | 348 | 431 | 286 | |
| | B | | 213 | 204 | 710 | 410 | |
| | C | | 195 | 464 | 322 | 319 | |
| | D | | 369 | 226 | 284 | 360 | |
| Toxicity Control | | | | | | | |
| | A | H9 cells cultured in | 115 | 196 | 162 | 228 | Neg |
| | B | 500 nmoles/ml PL | 168 | 260 | 540 | 229 | |
| | C | | 144 | 738 | 83 | 508 | |
| | D | | 2,688 | 418 | 101 | 269 | |
| Target Cell Control | | | | | | | |
| | A | H9 cells cultured in CM-1 | 454 | 167 | 408 | 392 | Neg |
| | B | | 245 | 529 | 817 | 398 | |
| | C | | 1,775 | 194 | 316 | 1,632 | |
| | D | | 180 | 233 | 485 | 894 | |

**N/A Not Available

B. Example of $TCID_{50}$ Calculation

| Group | Virus Dilution | No Pos | No Neg | Accumulated Values | | | % Positive |
|---|---|---|---|---|---|---|---|
| | | | | Positive | Negative | No Pos/Total | |
| Positive Control | $10^{-4}$ | 3 | 1 | 3 | 1 | 3/4 | 75 |
| | $10^{-5}$ | 0 | 4 | 0 | 5 | 0/5 | 0 |
| | $10^{-6}$ | 0 | 4 | 0 | 9 | 0/9 | 0 |
| | $10^{-7}$ | 0 | 4 | 0 | 13 | 0/13 | 0 |

$$4\left[\left(\frac{75+0+0+0}{100}\right)-0.5\right] \times \log \text{ of } 10$$

$4 - [0.75 - 0.5] \times 1$
$4 - [0.25] \times 1$
$4 - 0.25$
$TCID_{50}\ 10^{4.25}$ B. HIV-I in positive control cultures is calculated by the method of Reed and Muench statistical analysis (Am. J. Hygiene (1938) 27:493-497). An example is shown on Table B.

C. The test substance PL inhibited HIV-I replication of HIV-I infected H9 cells under the three conditions tested. The HIV-I virus used in the study had a titer of 4.25 $\log_{10}$ $TCID_{50}$/ml resulting in at least a 1.25 $\log_{10}$ $TCID_{50}$/ml of virus inhibition.

It is evident from the above results that by employing polyunsaturated carboxylic acid containing phosphatides, where the sn2 fatty acid is polyunsaturated, viral infection can be substantially inhibited. The above results demonstrate that in the presence of the subject phosphatides, the retrovirus HIV is specifically inhibited, while in the absence of the phosphatide, the retrovirus is able to demonstrate cytopathic effect in a normal manner. Thus, the subject invention provides an important adjunct in the treatment, both prophylactic and therapeutic, of viral infections, particularly retroviral infections.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for inhibiting proliferation of an HIV virus in a host cell, said method comprising:
    contacting said host cell with a viral proliferation inhibiting amount of a composition comprising at least one diacyl phosphatide of the formula:

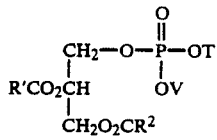

wherein:

T is a hydrogen, physiologically acceptable counterion, inositol, any of its phosphate derivatives, or other group which does not interfere with phospholipase $A_2$ activity;

V is a hydrogen or physiologically acceptable counterion;

$R'CO_2$ is a polyunsaturated aliphatic fatty acid of at least about 10 carbon atoms and not more than about 36 carbon atoms; and $R^2CO_2$ is an aliphatic fatty acid of at least 2 carbon atoms and not more than about 36 carbon atoms.

2. A method according to claim 1, wherein T is hydrogen, a physiologically acceptable counterion, inositol or phosphorylated derivatives thereof, choline, serine, ethanolamine, or glycerol.

3. A method according to claim 2, wherein $R'CO_2$ is of from 12 to 28 carbon atoms having from 2 to 4 sites of unsaturation.

4. A method according to claim 3, wherein $R'CO_2$ is linoleoyl.

5. A method according to claim 2, wherein $R'CO_2$ is of from 12 to 24 carbon atoms.

6. A method according to claim 2, wherein T is inositol or phosphorylated derivatives thereof.

7. A method according to claim 2, wherein said composition comprises vesicles, wherein said diacyl phosphatides are incorporated into the lipid layer of said vesicle.

8. A method according to claim 7, wherein said vesicle comprises a cytotoxic drug.

9. A method according to claim 7, wherein said vesicle comprises a ligand or receptor specific for a surface membrane protein bound to the surface of said vesicle.

10. A method according to claim 1, wherein said phosphatide is selected from 1-palmitoyl-2-linoleoyl phosphatidylinositol and 1-palmitoyl-2-linoleoyl phosphatidylcholine.

11. A method according to claim 1, wherein the acyl group at the sn2 position of said diacyl phosphatide is polyunsaturated.

12. A method according to claim 11, wherein said phosphatide is a plant phosphatide composition.

13. A method according to claim 1, wherein said composition further comprises a nonphosphatidyl lipid component which is a liposome and wherein said phosphatide is provided at a ratio of at least about 0.05:1.0 to said nonphosphatidyl lipid component.

14. A method according to claim 13, wherein said nonphosphatidyl lipid component is selected from cholesterol and polyunsaturated fatty acid esters.

15. A method according to claim 14, wherein said nonphosphatidyl lipid component is cholesterol.

16. A method according to claim 2, wherein $R'CO_2$ is from 12-28 carbon atoms, having from 2 to 6 sites of unsaturation.

17. A method according to claim 2, wherein $R'CO_2$ is linoleic acid, $R^2CO_2$ is palmitic acid, and T is selected from inositol or a phosphorylated derivative thereof.

18. A method according to claim 17, wherein T is inositol or a phosphorylated derivative thereof.

* * * * *